United States Patent
Loessner et al.

(10) Patent No.: US 11,339,386 B2
(45) Date of Patent: *May 24, 2022

(54) ENDOLYSIN POLYPEPTIDE

(71) Applicant: Micreos Human Health B.V., The Hague (NL)

(72) Inventors: Martin Johannes Loessner, Ebmatingen (CH); Fritz Eichenseher, Zürich (CH)

(73) Assignee: Micreos Human Health B.V., The Hague (NL)

(*) Notice: Subject to any disclaimer, the term of this patent is extended or adjusted under 35 U.S.C. 154(b) by 0 days.

This patent is subject to a terminal disclaimer.

(21) Appl. No.: 17/092,382

(22) Filed: Nov. 9, 2020

(65) Prior Publication Data

US 2021/0130802 A1    May 6, 2021

Related U.S. Application Data

(62) Division of application No. 15/759,883, filed as application No. PCT/EP2016/071405 on Sep. 12, 2016, now Pat. No. 10,829,749.

(30) Foreign Application Priority Data

Sep. 15, 2015   (EP) ..................... 15185337

(51) Int. Cl.
| | | |
|---|---|---|
| *A61K 39/00* | (2006.01) | |
| *C12N 9/36* | (2006.01) | |
| *C07K 14/31* | (2006.01) | |
| *A01N 43/50* | (2006.01) | |
| *A61K 38/47* | (2006.01) | |
| *A61K 38/00* | (2006.01) | |

(52) U.S. Cl.
CPC ........... *C12N 9/2462* (2013.01); *A01N 43/50* (2013.01); *A61K 38/47* (2013.01); *C07K 14/31* (2013.01); *C12Y 302/01017* (2013.01); *A61K 38/00* (2013.01)

(58) Field of Classification Search
CPC .................................................. C12N 9/2462
See application file for complete search history.

(56) References Cited

U.S. PATENT DOCUMENTS 10,829,749 B2 * 11/2020 Loessner ................ A61K 38/47

FOREIGN PATENT DOCUMENTS

WO    WO2012/150858 A1    11/2012

OTHER PUBLICATIONS

Trayer, H.R. and Buckley, C.E., 1970. Molecular properties of lysostaphin, a bacteriolytic agent specific for *Staphylococcus aureus*. Journal of Biological Chemistry, 245(18), pp. 4842-4846.
Recsei P A et al: "Cloning, sequence, and expression of the lysostaphin gene from *Staphylococcus simulans*", Proceedings of the National Academy of Sciences, National Academy of Sciences, US, vol. 84, No. 5, May 31, 1987 (May 31, 1987), pp. 1127-1131. [XP003007095].
Lu J.Z., Fujiwara, T., Komatsuzawa, H., Sugai, M. and Sakon, J., 2006. Cell wall-targeting domain of glycylglycine endopeptidase distinguishes among peptidoglycan cross-bridges. Journal of Biological Chemistry, 281(1), pp. 549-558.
Loessner, M.J., Kramer, K., Ebel, F. and Scherer, S., 2002. C-terminal domains of Listeria monocytogenes bacteriophage murein hydrolases determine specific recognition and high-affinity binding to bacterial cell wall carbohydrates. Molecular microbiology, 44(2), pp. 335-349.

* cited by examiner

*Primary Examiner* — Albert M Navarro
(74) *Attorney, Agent, or Firm* — N.V. Nederlandsch Octrooibureau

(57) ABSTRACT

The invention relates to the field of medicine, specifically to the field of treatment of conditions associated with *Staphylococcus* infection. The invention relates to a novel endolysin polypeptide specifically targeting a bacterial *Staphylococcus* cell. The invention further relates to said endolysin polypeptide for medical use, preferably for treating an individual suffering from a condition associated with *Staphylococcus* infection.

Figure 1:
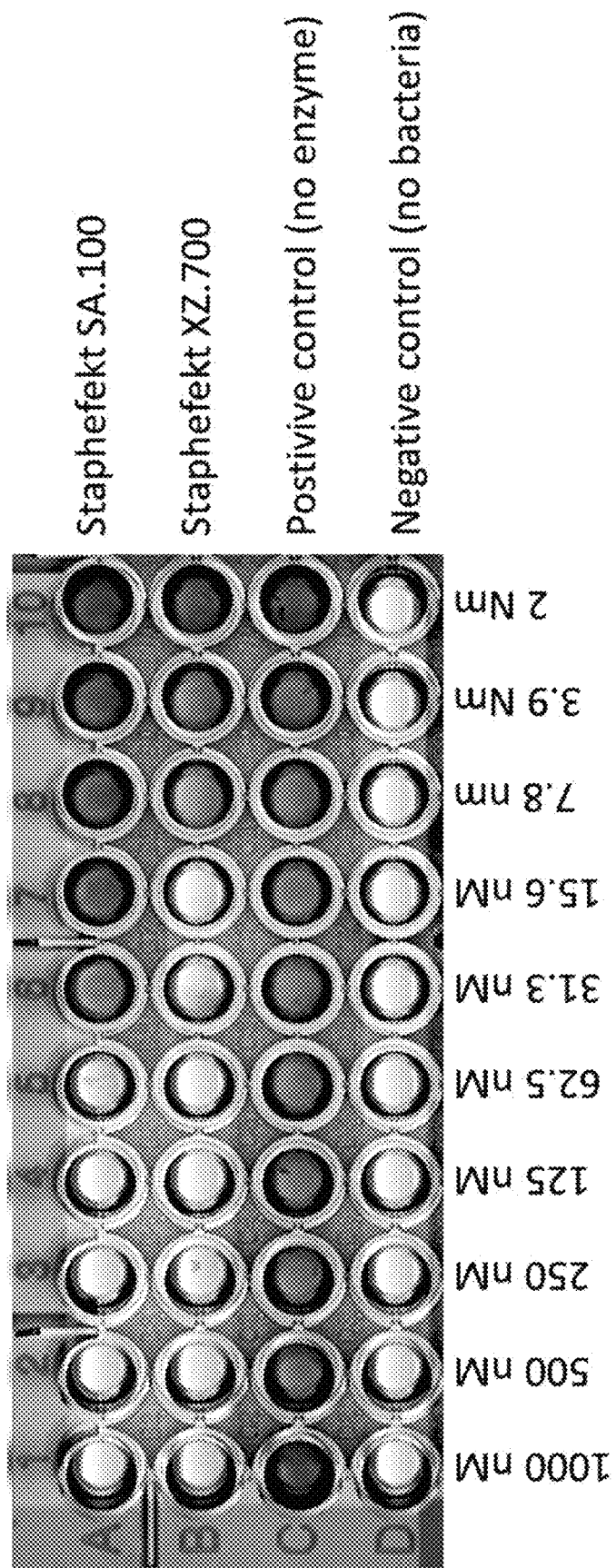

9 Claims, 3 Drawing Sheets
Specification includes a Sequence Listing.

ENDOLYSIN POLYPEPTIDE

FIELD OF THE INVENTION

The invention relates to the field of medicine, specifically to the field of treatment of conditions associated with *Staphylococcus* infection. The invention relates to a novel endolysin polypeptide specifically targeting a bacterial *Staphylococcus* cell. The invention further relates to said endolysin polypeptide for medical use, preferably for treating an individual suffering from a condition associated with *Staphylococcus* infection.

BACKGROUND OF THE INVENTION

*Staphylococcus aureus* is a major animal pathogen, especially in mammals such as humans and cows, which is frequently implicated in several serious infectious diseases and food poisoning. Its treatment becomes more and more difficult because of emerging antibiotic resistant strains. Endolysins from phages infecting *Staphylococcus aureus* have been shown to potentially control these pathogens and can be used for their specific detection. In most cases, major obstacles in the application of endolysins targeting *Staphylococcus* species are low enzyme activity, difficult production in large quantities and/or protein stability. Accordingly, there is a need for an endolysin polypeptide with improved characteristics on for example antimicrobial activity, stability and/or reduced immunogenicity.

SUMMARY OF THE INVENTION

The invention relates to an endolysin polypeptide specific for *Staphylococcus*, said polypeptide comprising:

a polypeptide with an amino acid sequence that has at least 80% sequence identity with SEQ ID NO: 2, or a polypeptide with an amino acid sequence that has at least 80% sequence identity with SEQ ID NO: 1 and having a truncation of at least 5, 10, 20, 30, or 40 amino acids in the region of amino acids 156 to 199 of SEQ ID NO: 1.

The invention further relates to an endolysin polypeptide with an amino acid sequence according to SEQ ID NO: 2.

The invention further relates to a polynucleotide encoding an endolysin polypeptide according to the invention. The invention further relates to a nucleic acid construct comprising a polynucleotide according to the invention. The invention further relates to an expression vector comprising a nucleic acid construct according to the invention.

The invention further relates to a host cell comprising a polynucleotide according to the invention, a nucleic acid construct according to the invention or an expression construct according to the invention.

The invention further relates to a method for the production of an endolysin polypeptide according to the invention, comprising:

culturing a host cell according to the invention under conditions conducive to the production of the endolysin polypeptide, optionally isolating and purifying the endolysin polypeptide from the culture broth, and optionally freeze-drying the endolysin polypeptide.

The invention further relates to a method for producing an endolysin polypeptide according to the invention with enhanced activity comprising dialysis of an endolysin according to the invention, or an endolysin polypeptide obtainable by a method according to the invention, said dialysis comprising the steps of:

i) dialysis against a buffer comprising a chelating compound, and ii) dialysis against a divalent metal ion-containing buffer, preferably a divalent metal ion selected form the group consisting of $Co^{2+}$, $Cu^{2+}$, $Mg^{2+}$, $Ca^{2+}$, $Mn^{2+}$ and $Zn^{2+}$.

The invention further relates to a composition comprising an endolysin polypeptide according to the invention, or an endolysin polypeptide obtainable by a method according to the invention, or a polynucleotide according to the invention, or a nucleic acid construct according to the invention, or an expression construct according to the invention, or a host cell according to the invention.

The invention further relates to pharmaceutical composition comprising an endolysin polypeptide according to the invention, or an endolysin polypeptide obtainable by a method according to the invention, or a polynucleotide according to the invention, or a nucleic acid construct according to the invention, or an expression construct according to the invention, or a host cell according to the invention, said pharmaceutical composition further comprising a pharmaceutically acceptable excipient.

The invention further relates to a composition according to invention, further comprising an additional active ingredient.

The invention further relates to a composition according to the invention, for use as a medicament.

The invention further relates to a composition according to the invention, for use as a medicament in the treatment of a condition associated with infection with a *Staphylococcus*.

The invention further relates to a method of treatment of a condition associated with infection with a *Staphylococcus*, comprising administration an endolysin polypeptide according to the invention, or an endolysin polypeptide obtainable by a method according to the invention, or a polynucleotide according to the invention, or a nucleic acid construct according to the invention, or an expression construct according to the invention, or a host cell according to the invention, or a composition according to the invention.

The invention further relates to the use of an endolysin polypeptide according to the invention, or an endolysin polypeptide obtainable by a method according to the invention, or a polynucleotide according to the invention, or a nucleic acid construct according to the invention, or an expression construct according to the invention, or a host cell according to the invention, or a composition according to the invention, as an antimicrobial, preferably as a food additive or a disinfectant.

The invention further relates to the use of a an endolysin polypeptide according to the invention, or an endolysin polypeptide obtainable by a method according to the invention, or a polynucleotide according to the invention, or a nucleic acid construct according to the invention, or an expression construct according to the invention, or a host cell according to the invention, or a composition according to the invention, for detecting a *Staphylococcus*, preferably in a diagnostic application.

DETAILED DESCRIPTION OF THE INVENTION

Surprisingly, a novel endolysin polypeptide with enhanced specific activity and reduced immunogenicity was arrived at by the inventors.

Accordingly, in a first aspect, the present invention provides for an endolysin polypeptide specific for *Staphylococcus*, said polypeptide comprising:

a polypeptide with an amino acid sequence that has at least 80% sequence identity with SEQ ID NO: 2, or a polypeptide with an amino acid sequence that has at least 80% sequence identity with SEQ ID NO: 1 and having a truncation of at least 5, 10, 20, 30, or 40 amino acids in the region of amino acids 156 to 199 of SEQ ID NO: 1.

Said endolysin polypeptide herein referred to as an endolysin polypeptide according to the invention. Preferably, said endolysin polypeptide according to the invention has enhanced specific activity and/or reduced immunogenicity than an endolysin polypeptide with the amino acid sequence according to SEQ ID NO: 1. More preferably, said endolysin polypeptide according to the invention has enhanced specific activity and reduced immunogenicity than an endolysin polypeptide with the amino acid sequence according to SEQ ID NO: 1. Preferably, the endolysin polypeptide according to the invention comprises a polypeptide with an amino acid sequence that has at least 81%, 82%, 83%, 84%, 85%, 86%, 87%, 88%, 89%, 90%, 91%, 92%, 93%, 94%, 95%, 96%, 97%, 98%, 99% or more preferably 100% sequence identity with SEQ ID NO: 2. More preferably, the endolysin polypeptide according to the invention consists of a polypeptide with an amino acid sequence that has at least 81%, 82%, 83%, 84%, 85%, 86%, 87%, 88%, 89%, 90%, 91%, 92%, 93%, 94%, 95%, 96%, 97%, 98%, 99% or more preferably 100% sequence identity with SEQ ID NO: 2.

Preferably, the endolysin polypeptide according to the invention comprises a polypeptide with an amino acid sequence that has at least 80%, 81%, 82%, 83%, 84%, 85%, 86%, 87%, 88%, 89%, 90%, 91%, 92%, 93%, 94%, 95%, 96%, 97%, 98%, or more preferably at least 99% sequence identity with SEQ ID NO: 1 and having a truncation of at least 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39 or more preferably at least 40 amino acids in the region of amino acids 156 to 199 of SEQ ID NO: 1. Herein, the term truncation may also be referred to as an internal truncation or as a deletion.

A more preferred endolysin polypeptide according to invention has an amino acid sequence according to SEQ ID NO: 2.

Within the context of the invention, an endolysin polypeptide specific for *Staphylococcus* is construed as a polypeptide that has lytic activity for *Staphylococcus*, preferably said lytic activity is peptidoglycan hydrolase activity for *Staphylococcus* peptidoglycan. Preferably, said *Staphylococcus* is selected from the group consisting of *S. aureus, S. simulans* and *S. carnosus*. Lytic activity can be assessed by any suitable method known to the person skilled in the art. Preferably, one of the assays as described in the examples herein is used.

Encompassed within the invention are endolysin polypeptides that comprise an endolysin according to the invention or a functional part thereof as a backbone and further comprises a further polypeptide or a functional part thereof. Said further polypeptide of a functional part thereof may e.g. be, but is not limited to a lytic domain or an amidase domain. Such further polypeptide or functional part thereof may he native of may be heterologous to the endolysin polypeptide according to the invention.

An endolysin polypeptide according to the invention may be derived from one of the sequences herein by substituting, inserting, deleting, or adding one, 2, 3, 4, 5, 6, 7, 8, 9, 10, 12, 14, 16, 18, 20 or more nucleotides or amino acids, respectively. An endolysin polypeptide according to the invention may be derived from one of the sequences as identified herein by adding an additional N- or C-terminal amino acids or chemical moieties to increase stability, solubility and activity.

An endolysin polypeptide according to the invention may have a length of at least 300, 350, 400 or 450 amino acids, preferably 462 amino acids, and/or at most 1500, 1400, 1300, 1200, 1100, 1000, 900, 800, 700, 600, 500 or 462 amino acids. Preferably, said polypeptide has a length of at least 400, 410, 420, 430, 440, 450, 460, 462, 470, 480, 490, 500, 510 or 520 amino acids and/or at most 1500, 1400, 1300, 1200, 1100, 1000, 900, 800, 700, 600 amino acids. An embodiment of the invention encompasses a variant endolysin polypeptide according to the invention. A variant endolysin polypeptide may be any non-naturally occurring form of the endolysin polypeptide according to the invention. An endolysin polypeptide variant may differ in some engineered way from SEQ DI NO: 2. A variant endolysin polypeptide according to the invention may be made by site-directed mutagenesis starting from the nucleotide sequence of SEQ ID NO: 1 or SEQ ID NO: 2. Preferably, a variant endolysin polypeptide according to the invention contains mutations that do not alter the biological function of the encoded polypeptide; preferably, a variant endolysin polypeptide according to the invention exhibits *Staphylococcus* peptidoglycan cell wall-binding and/or a lytic activity which is the same or enhanced as compared to the endolysin polypeptide with the amino acid sequence according to SEQ ID NO: 2.

An endolysin polypeptide according to the invention may comprise a tag for e.g. ease of purification. Preferably, said tag is selected from, but is not limited to, the group consisting of a FLAG-tag, poly(His)-tag, HA-tag and Myc-tag, more preferably said tag is a 6× His-tag.

In a second aspect, the invention provides for (claim 3) apolynucleotide encoding an endolysin polypeptide according to the first aspect of the invention. Preferably, such polynucleotide according to the invention is coding optimized for efficient expression in a specific host. The person skilled in the art knows how to optimize codons and/or codon pairs. A polynucleotide according to the invention may be an RNA or DNA molecule, preferably a DNA molecule.

The invention further relates to a nucleic acid construct comprising a polynucleotide according to the invention.

The invention further relates to an expression vector comprising a nucleic acid construct or a polynucleotide according to the invention. An expression vector according to the invention may be a recombinant expression vector. Such vector may constitute a plasmid, a cosmid, a bacteriophage or a virus, or a part thereof, which is transformed by introducing a nucleic acid construct or a polynucleotide according to the invention. Such transformation vectors specific to the host organism to be transformed are well known to those skilled in the art and widely described in the literature. In order to produce a polynucleotide or endolysin polypeptide according to the invention in a host, a process for the transformation of a host organism, and integration of a polynucleotide, nucleic acid construct or expression vector according to the invention may be appropriate. Such transformation may be carried out by any suitable known means which have been widely described in the specialist literature and are well-known to the person skilled in the art.

In a third aspect, the invention relates to a host cell comprising a polynucleotide according to the invention, a nucleic acid construct according to the invention or an expression construct according to the invention. A host cell according to the invention may be any microbial, prokaryotic or eukaryotic, cell which is suitable for expression of the polypeptide of the invention. Preferably, said cell is an *E. coli*. In an even more preferred embodiment, said cell is *E. coli* XL1blue MRF.

In a fourth aspect, the invention provides for a method for the production of an endolysin polypeptide according to the invention, comprising:

culturing a host cell according to the invention under conditions conducive to the production of the endolysin polypeptide, optionally isolating and purifying the endolysin polypeptide from the culture broth, and optionally freeze-drying the endolysin polypeptide.

Preferably, an *E. coli* is used in the method for producing an endolysin polypeptide according to the invention. More preferably an *E. coli* XL1blueMRF is used in step i) for producing an endolysin polypeptide according to the invention. Preferably, in the step of isolation and purification, IMAC and Econo-Pac Chromatography columns (Biorad) packed with 5 mL low density Nickel chelating agarose beads (ABT beads) in combination with gravity flow are used to purify an endolysin polypeptide according to the invention. The eluted polypeptide can be dialyzed for 2, 4, and 12 hours against 3×1l lyophilization buffer, said buffer preferably comprising 50 mM phosphate, 500 mM sucrose, 200 mM mannitol, 0.005% polysorbate20, pH 7.4.

Lyophilisation and reconstitution are preferably construed as dehydration by freeze-drying and subsequent reconstitution of the sample by adding water. Preferably, lyophilisation and reconstitution is performed by dialyzing against 3 changes of 300 ml lyophilization buffer (50 mM phosphate or Tris, 500 mM sucrose, 200 mM mannitol, pH 7.4) aliquot and freezing in the gaseous phase of liquid nitrogen. Freeze-drying is preferably performed under standard conditions, preferably at −40° C. and vacuum at 75 mTorr for 60 minutes, followed by increasing the temperature during 5 hours to −10° C. and another 60 minutes at −10° C. at the same vacuum levels. As a final step, the temperature is preferably increased to 25° C. during 10 hours. Samples are reconstituted by the addition of water.

The invention also provides for a (claim 8) method for producing an endolysin polypeptide according to the invention with enhanced activity comprising dialysis of an endolysin polypeptide according to the first aspect of the invention, or an endolysin polypeptide obtainable by a method depicted here above, said dialysis comprising the steps of:

i) dialysis against a buffer comprising a chelating compound, and ii) dialysis against a divalent metal ion-containing buffer, preferably a divalent metal ion selected form the group consisting of $Co^{2+}$, $Cu^{2+}$, $Mg^{2+}$, $Ca^{2+}$, $Mn^{2+}$ and $Zn^{2+}$.

A "chelating compound" is defined herein as a compound that binds a metal ion. Well known chelating compounds are ethylene diamine tetra-acetic acid (EDTA) and ethylene glycol tetra-acetic acid (EGTA). Preferably EDTA is used in step i) of the method of the invention.

Preferably, the divalent metal ion of step ii) is selected from the group consisting $Mg^{2+}$, $Ca^{2+}$, $Mn^{2+}$, $Co^{2+}$ and $Cu^{2+}$, more preferably, said divalent metal ion is selected from the group consisting of $Mg^{2+}$, $Ca^{2+}$, $Mn^{2+}$ and $Co^{2+}$, even more preferably said divalent metal ion is $Mg^{2+}$ or $Ca^{2+}$.

Substituting a divalent metal ion by any of $Co^{2+}$, $Cu^{2+}$, $Mg^{2+}$, $Ca^{2+}$, $Mn^{2+}$ and $Zn^{2+}$ will preferably result in an increase of a lytic activity of an endolysin polypeptide according to the invention. Lytic activity is assessed as defined elsewhere herein. Preferably, this method according to the invention leads to an increase in a lytic activity of at least 1.1, 1.2, 1.3, 1.4, 1.5, 1.6, 1.7, 1.8, 1.9 or 2 fold as compared to the corresponding untreated polypeptide. Even more preferably, the method leads to an increase in lytic activity of at least 2.5 fold. Preferably, the treated polypeptide exhibits a 0.7, 0.8, 0.9, 1.0, 1.1, 1.2, 1.3, 1.4, 1.5, 1.6, 1.7, 1.8, 1.9 to 2 fold increase in lytic activity as compared to the untreated polypeptide with the amino acid sequence according to SEQ ID NO: 2.

In a fifth aspect, the invention provides for a composition comprising an endolysin polypeptide according to the invention, or an endolysin polypeptide obtainable by a method according to the invention, or a polynucleotide according to the invention, or a nucleic acid construct according to the invention, or an expression construct according to the invention, or a host cell according to the invention. Such composition according to the invention preferably exhibits lytic activity lytic for *Staphylococcus*, preferably said lytic activity is peptidoglycan hydrolase activity for *Staphylococcus* peptidoglycan. Preferably, said *Staphylococcus* is selected from the group consisting of *S. aureus*, *S. simulans* and *S. carnosus*. A composition according to the present invention may comprise a mixture of different polynucleotides, and/or nucleic acid constructs and/or endolysin polypeptides an/or vectors and/or cells according to the invention or obtainable by a method according to the invention.

A composition according to the invention may further comprise a pharmaceutically acceptable excipient. Such composition is herein referred to as a pharmaceutical composition and is preferably for use as a medicine or as a medicament. Preferably the medicament is used in the treatment of infectious diseases.

Accordingly, there is provided a pharmaceutical composition comprising an endolysin polypeptide according to the invention, or an endolysin polypeptide obtainable by a method according to the invention, or a polynucleotide according to the invention, or a nucleic acid construct according to the invention, or an expression construct according to the invention, or a host cell according to the invention, said pharmaceutical composition further comprising a pharmaceutically acceptable excipient.

A composition according to the invention may further comprise one or more additional active ingredients. Active preferably defined as showing a lytic activity as defined elsewhere herein. Preferably, said one or more additional active ingredients are selected from the group consisting of a bacteriophage or phage, a phage endolysin derived from such phage and an antibiotic. A phage encompassed herein can be any phage known in literature. Preferably, such phage is, but is not limited, from a family of the list consisting of Myoviridae, Siphoviridae and Podoviridae. Such phage may also be from a family of the list consisting of Tectiviridae, Corticoviridae, Lipothrixviridae, Plasmaviridae, Rudiviridae, Fuselloviridae, Inoviridae, Microviridae, Leviviridae and Cystoviridae. Within the context of the invention, a combination of active ingredients as defined herein can be administered sequentially or simultaneously. A composition according to the invention may be in the liquid, solid or semi-liquid or semi-solid form.

A composition according to the invention can be used to treat animals, including humans, infected with *Staphylococcus*, preferably *S. aureus*. Any suitable route of administration can be used to administer said composition including but not limited to: oral, aerosol or other device for delivery to the lungs, nasal spray, intravenous, intramuscular, intraperitoneal, intrathecal, vaginal, rectal, topical, lumbar puncture, intrathecal, and direct application to the brain and/or meninges.

A composition according to the invention comprising a polynucleotide or a nucleic acid construct or an endolysin polypeptide or a vector or a cell according to the invention or obtainable by a method according to the invention is preferably said to be active, functional or therapeutically active or able to treat, prevent and/or delay an infectious disease when it decreases the amount of a *Staphylococcus* species present in a patient or in a cell of said patient or in a cell line or in a cell free in vitro system and preferably means that 99%, 90%, 80%, 70%, 60%, 50%, 40%, 30%, 20%, 10%, 5% or less of the initial amount of a *Staphylococcus* species, is still detectable after treatment. Preferably no *Staphylococcus* species is detectable after treatment. In this paragraph, the expression "amount of *Staphylococcus* species" preferably means alive *Staphylococcus* genera. *Staphylococcus* species may be detected using standard techniques known by the artisan such as immunohistochemical techniques using *Staphylococcus* specific antibodies, tube coagulase tests that detect staphylocoagulase or "free coagulase", detection of surface proteins such as clumping factor (slide coagulase test) and/or protein A (commercial latex tests). Alive *Staphylococcus* species may be detected using standard techniques known by the artisan such as microbiological bacterial culture techniques and/or real-time quantitative reverse transcription polymerase chain reaction to assay for bacterial mRNA. Said decrease is preferably assessed in a tissue or in a cell of an individual or a patient by comparison to the amount present in said individual or patient before treatment with said composition or polypeptide according to the invention. Alternatively, the comparison can be made with a tissue or cell of said individual or patient which has not yet been treated with said composition or polypeptide in case the treatment is local.

A composition comprising a polynucleotide or a nucleic acid construct or a polypeptide or a vector or a cell according to the invention or obtainable by a method according to the invention may be administered to a subject in need thereof or of a cell, tissue or organ or said patient at least one week, one month, six month, one year or more.

Accordingly, the invention provides for a composition according to the invention, for use as a medicament for the treatment of a subject in need thereof. Preferably, said composition is for use as a medicament in the treatment of a condition associated with infection of a subject with a *Staphylococcus*, preferably a bacterium of the species *S. aureus*.

The invention further provides for a method of treatment, delay and/or prevention of a condition associated with infection of a subject with a *Staphylococcus*, preferably a bacterium of the species *S. aureus*, comprising administration an endolysin polypeptide according the invention, or an endolysin polypeptide obtainable by a method according to the invention, or a polynucleotide according to the invention, or a nucleic acid construct according to the invention, or an expression construct according to the invention, or a host cell according to the invention, or a composition according to the invention.

The medical use herein described may be formulated as a product according to the invention for use as a medicament for treatment of the stated diseases but could equally be formulated as a method of treatment of the stated diseases using a product according to the invention, a product according to the invention for use in the preparation of a medicament to treat the stated diseases and use of a product according to the invention for the treatment of the stated diseases. Such medical uses are all envisaged by the present invention. The subject in need of treatment, delay and/or prevention of a condition associated with infection may by any animal subject, preferably a mammal, more preferably cattle, domestic animals like a dog or a cat, or a human subject.

The endolysin polypeptide according the invention, or an endolysin polypeptide obtainable by a method according to the invention, or a polynucleotide according to the invention, or a nucleic acid construct according to the invention, or an expression construct according to the invention, or a host cell according to the invention, or a composition according to the invention may conveniently be used in a method for combination treatment of atopic dermatitis as presented in WO2015/005787 wherein anti-inflammatory compound and a compound specifically targeting a bacterial cell, preferably a gram positive bacterial cell are used to treat atopic dermatitis or eczema. The compound specifically targeting a bacterial cell can conveniently be an endolysin polypeptide obtainable by a method according to the invention, or a polynucleotide according to the invention, or a nucleic acid construct according to the invention, or an expression construct according to the invention, or a host cell according to the invention, or a composition according to the invention.

The endolysin polypeptide according the invention, or an endolysin polypeptide obtainable by a method according to the invention, or a polynucleotide according to the invention, or a nucleic acid construct according to the invention, or an expression construct according to the invention, or a host cell according to the invention, or a composition according to the invention may conveniently be used in a method of treatment of an intracellular bacterial infection in a subject in need thereof, comprising:

administration of an effective amount of an agent that increases the intracellular pH of a host cell and/or of an intracellular compartment of a host cell, and administration of an effective amount of a bactericidal agent. Said method is herein referred to as a method according to the invention, wherein preferably, the increase in pH activates a non-replicating intracellular bacterium and the bactericidal agent kills the activated intracellular bacterium. Such method of treatment is described in EP15158880.3. The bactericidal agent can conveniently be an endolysin polypeptide obtainable by a method according to the invention, or a polynucleotide according to the invention, or a nucleic acid construct according to the invention, or an expression construct according to the invention, or a host cell according to the invention, or a composition according to the invention. Preferably, the endolysin polypeptide according to the invention comprises a protein transduction domain enabling the endolysin polypeptide to enter the cell that harbors the intracellular bacterium. Protein transduction domains are extensively described in EP15158880.3.

In an aspect, the invention relates to a non-medical composition exhibiting lytic activity as defined elsewhere herein. Preferably, this embodiment relates to an antimicrobial. Preferably, this embodiment relates to an antimicrobial for lysing a bacterium, preferably a bacterium of the genus *Staphylococcus*, more preferably a bacterium of the species *S. aureus*. Preferably this embodiment relates to an antimicrobial as food preservative or disinfectant.

Accordingly, there is provided the use of an endolysin polypeptide according to the invention, or an endolysin polypeptide obtainable by a method according to the invention, or a polynucleotide according to the invention, or a nucleic acid construct according to the invention, or an expression construct according to the invention, or a host cell according to the invention, or a composition according to the invention, as an antimicrobial, preferably as a food additive or a disinfectant. Examples of such use are, but are not limited to, rinsing the cups of a milking device with a composition according to the invention before milking to prevent transmission of *Staphylococci* from cow to cow, cleaning of surfaces in food industry and cleaning chirurgical tools. Such use can be combined with any sterilization method or disinfectant known in the art such as ultrasonic cleaning, irradiation or thermal sterilization, by immersing the equipment in a disinfectant solution such as ethanol, ammonium, iodine and/or aldehyde disinfectant, or by using gas sterilization by retaining the device in a closed atmosphere such as formalin gas or ethylene oxide gas.

The invention further relates to an endolysin polypeptide according to the invention, or an endolysin polypeptide obtainable by a method according to the invention, or a polynucleotide according to the invention, or a nucleic acid construct according to the invention, or an expression construct according to the invention, or a host cell according to the invention, or a composition according to the invention, for detecting a *Staphylococcus*, preferably *S. aureus*, preferably in a diagnostic application.

Definitions

"Sequence identity" is herein defined as a relationship between two or more amino acid (peptide, polypeptide, or protein) sequences or two or more nucleic acid (nucleotide, polynucleotide) sequences, as determined by comparing the sequences. In the art, "identity" also means the degree of sequence relatedness between amino acid or nucleotide sequences, as the case may be, as determined by the match between strings of such sequences. "Similarity" between two amino acid sequences is determined by comparing the amino acid sequence and its conserved amino acid substitutes of one peptide or polypeptide to the sequence of a second peptide or polypeptide. In a preferred embodiment, identity or similarity is calculated over the whole SEQ ID NO as identified herein. "Identity" and "similarity" can be readily calculated by known methods, including but not limited to those described in Computational Molecular Biology, Lesk, A. M., ed., Oxford University Press, New York, 1988; Biocomputing: Informatics and Genome Projects, Smith, D. W., ed., Academic Press, New York, 1993; Computer Analysis of Sequence Data, Part I, Griffin, A. M., and Griffin, H. G., eds., Humana Press, New Jersey, 1994; Sequence Analysis in Molecular Biology, von Heine, G., Academic Press, 1987; and Sequence Analysis Primer, Gribskov, M. and Devereux, J., eds., M Stockton Press, New York, 1991; and Carillo, H., and Lipman, D., SIAM J. Applied Math., 48:1073 (1988).

Preferred methods to determine identity are designed to give the largest match between the sequences tested. Methods to determine identity and similarity are codified in publicly available computer programs. Preferred computer program methods to determine identity and similarity between two sequences include e.g. the GCG program package (Devereux, J., et al., Nucleic Acids Research 12 (1): 387 (1984)), BestFit, BLASTP, BLASTN, and FASTA (Altschul, S. F. et al., J. Mol. Biol. 215:403-410 (1990). The BLAST X program is publicly available from NCBI and other sources (BLAST Manual, Altschul, S., et al., NCBI NLM NIH Bethesda, Md. 20894; Altschul, S., et al., J. Mol. Biol. 215:403-410 (1990). The well-known Smith Waterman algorithm may also be used to determine identity.

Preferred parameters for polypeptide sequence comparison include the following: Algorithm: Needleman and Wunsch, J. Mol. Biol. 48:443-453 (1970); Comparison matrix: BLOSSUM62 from Hentikoff and Hentikoff, Proc. Natl. Acad. Sci. USA. 89:10915-10919 (1992); Gap Penalty: 12; and Gap Length Penalty: 4. A program useful with these parameters is publicly available as the "Ogap" program from Genetics Computer Group, located in Madison, Wis. The aforementioned parameters are the default parameters for amino acid comparisons (along with no penalty for end gaps). Preferred parameters for nucleic acid comparison include the following: Algorithm: Needleman and Wunsch, J. Mol. Biol. 48:443-453 (1970); Comparison matrix: matches=+10, mismatch=0; Gap Penalty: 50; Gap Length Penalty: 3. Available as the Gap program from Genetics Computer Group, located in Madison, Wis. Given above are the default parameters for nucleic acid comparisons.

Optionally, in determining the degree of amino acid similarity, the skilled person may also take into account so-called "conservative" amino acid substitutions, as will be clear to the skilled person. Conservative amino acid substitutions refer to the interchangeability of residues having similar side chains. For example, a group of amino acids having aliphatic side chains is glycine, alanine, valine, leucine, and isoleucine; a group of amino acids having aliphatic-hydroxyl side chains is serine and threonine; a group of amino acids having amide-containing side chains is asparagine and glutamine; a group of amino acids having aromatic side chains is phenylalanine, tyrosine, and tryptophan; a group of amino acids having basic side chains is lysine, arginine, and histidine; and a group of amino acids having sulphur-containing side chains is cysteine and methionine. Preferred conservative amino acids substitution groups are: valine-leucine-isoleucine, phenylalanine-tyrosine, lysine-arginine, alanine-valine, and asparagine-glutamine. Substitutional variants of the amino acid sequence disclosed herein are those in which at least one residue in the disclosed sequences has been removed and a different residue inserted in its place. Preferably, the amino acid change is conservative. Preferred conservative substitutions for each of the naturally occurring amino acids are as follows: Ala to ser; Arg to lys; Asn to gln or his; Asp to glu; Cys to ser or ala; Gln to asn; Glu to asp; Gly to pro; His to asn or gln; Ile to leu or val; Leu to ile or val; Lys to arg; gln or glu; Met to leu or ile; Phe to met, leu or tyr; Ser to thr; Thr to ser; Trp to tyr; Tyr to trp or phe; and, Val to ile or leu.

A "nucleic acid molecule" or "polynucleotide" (the terms are used interchangeably herein) is represented by a nucleotide sequence. A "polypeptide" is represented by an amino acid sequence. A "nucleic acid construct" is defined as a nucleic acid molecule which is isolated from a naturally occurring gene or which has been modified to contain segments of nucleic acids which are combined or juxtaposed in a manner which would not otherwise exist in nature. A nucleic acid molecule is represented by a nucleotide sequence. Optionally, a nucleotide sequence present in a nucleic acid construct is operably linked to one or more control sequences, which direct the production or expression of said peptide or polypeptide in a cell or in a subject.

"Operably linked" is defined herein as a configuration in which a control sequence is appropriately placed at a position relative to the nucleotide sequence coding for the polypeptide of the invention such that the control sequence directs the production/expression of the peptide or polypeptide of the invention in a cell and/or in a subject. "Operably linked" may also be used for defining a configuration in which a sequence is appropriately placed at a position relative to another sequence coding for a functional domain such that a chimeric polypeptide is encoded in a cell and/or in a subject.

"Expression" is construed as to include any step involved in the production of the peptide or polypeptide including, but not limited to, transcription, post-transcriptional modification, translation, post-translational modification and secretion.

A "control sequence" is defined herein to include all components which are necessary or advantageous for the expression of a polypeptide. At a minimum, the control sequences include a promoter and transcriptional and translational stop signals. Optionally, a promoter represented by a nucleotide sequence present in a nucleic acid construct is operably linked to another nucleotide sequence encoding a peptide or polypeptide as identified herein.

The term "transformation" refers to a permanent or transient genetic change induced in a cell following the incorporation of new DNA (i.e. DNA exogenous to the cell). When the cell is a bacterial cell, as is intended in the present invention, the term usually refers to an extrachromosomal, self-replicating vector which harbors a selectable antibiotic resistance.

An "expression vector" may be any vector which can be conveniently subjected to recombinant DNA procedures and can bring about the expression of a nucleotide sequence encoding a polypeptide of the invention in a cell and/or in a subject. As used herein, the term "promoter" refers to a nucleic acid fragment that functions to control the transcription of one or more genes or nucleic acids, located upstream with respect to the direction of transcription of the transcription initiation site of the gene. It is related to the binding site identified by the presence of a binding site for DNA-dependent RNA polymerase, transcription initiation sites, and any other DNA sequences, including, but not limited to, transcription factor binding sites, repressor and activator protein binding sites, and any other sequences of nucleotides known to one skilled in the art to act directly or indirectly to regulate the amount of transcription from the promoter. Within the context of the invention, a promoter preferably ends at nucleotide −1 of the transcription start site (TSS).

A "polypeptide" as used herein refers to any peptide, oligopeptide, polypeptide, gene product, expression product, or protein. A polypeptide is comprised of consecutive amino acids. The term "polypeptide" encompasses naturally occurring or synthetic molecules. The sequence information as provided herein should not be so narrowly construed as to require inclusion of erroneously identified bases. The skilled person is capable of identifying such erroneously identified bases and knows how to correct for such errors.

In this document and in its claims, the verb "to comprise" and its conjugations is used in its non-limiting sense to mean that items following the word are included, but items not specifically mentioned are not excluded. In addition the verb "to consist" may be replaced by "to consist essentially of" meaning that a product or a composition or a nucleic acid molecule or a peptide or polypeptide of a nucleic acid construct or vector or cell as defined herein may comprise additional component(s) than the ones specifically identified; said additional component(s) not altering the unique characteristic of the invention. In addition, reference to an element by the indefinite article "a" or "an" does not exclude the possibility that more than one of the elements is present, unless the context clearly requires that there be one and only one of the elements. The indefinite article "a" or "an" thus usually means "at least one".

All patent and literature references cited in the present specification are hereby incorporated by reference in their entirety.

The following examples are offered for illustrative purposes only, and are not intended to limit the scope of the present invention in any way.

FIGURE LEGENDS

FIG. 1. Representative image of minimal inhibitory concentrations (MIC) of an endolysin polypeptide according to the invention.

Figure 2A:
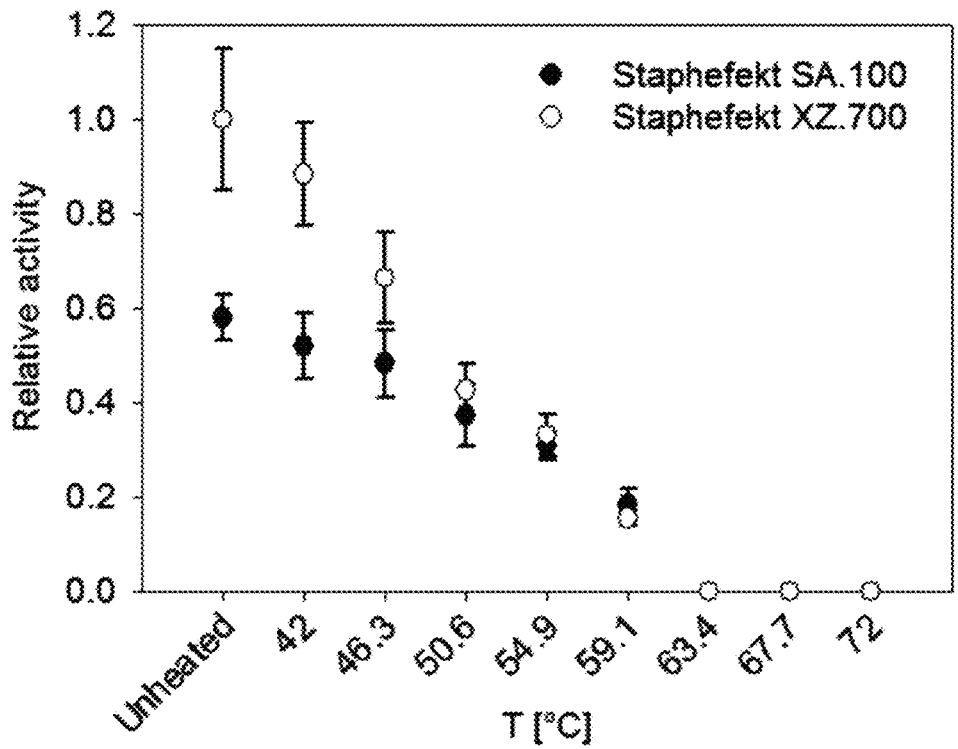
Figure 2B:
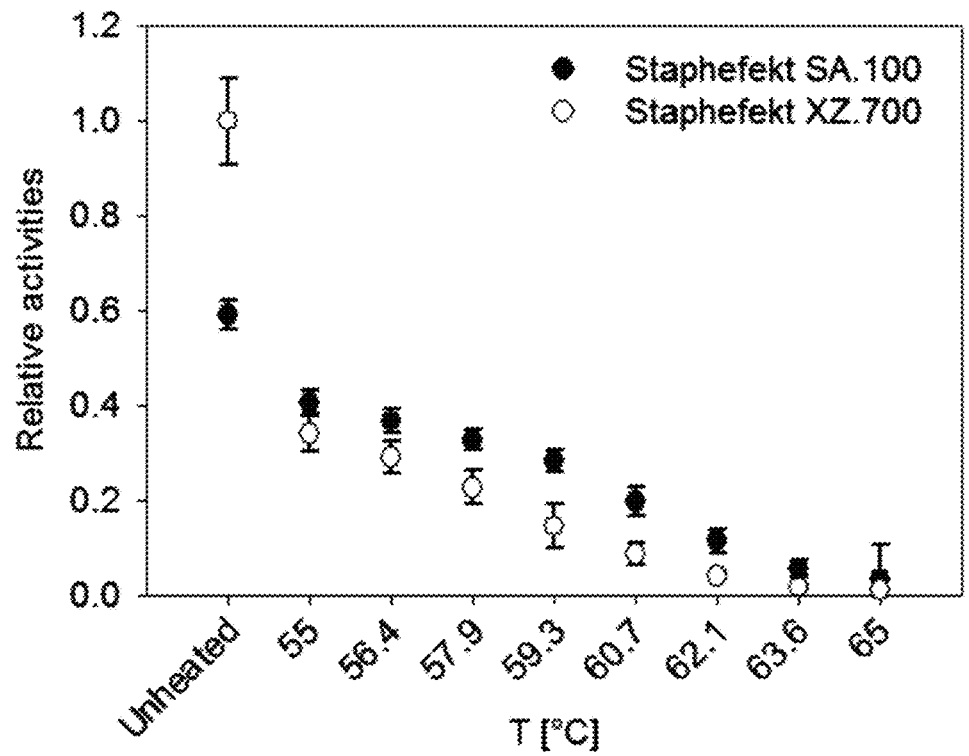

FIG. 2A and FIG. 2B. Thermal stability and specific activity of endolysin polypeptide according to the invention.

Figure 3:
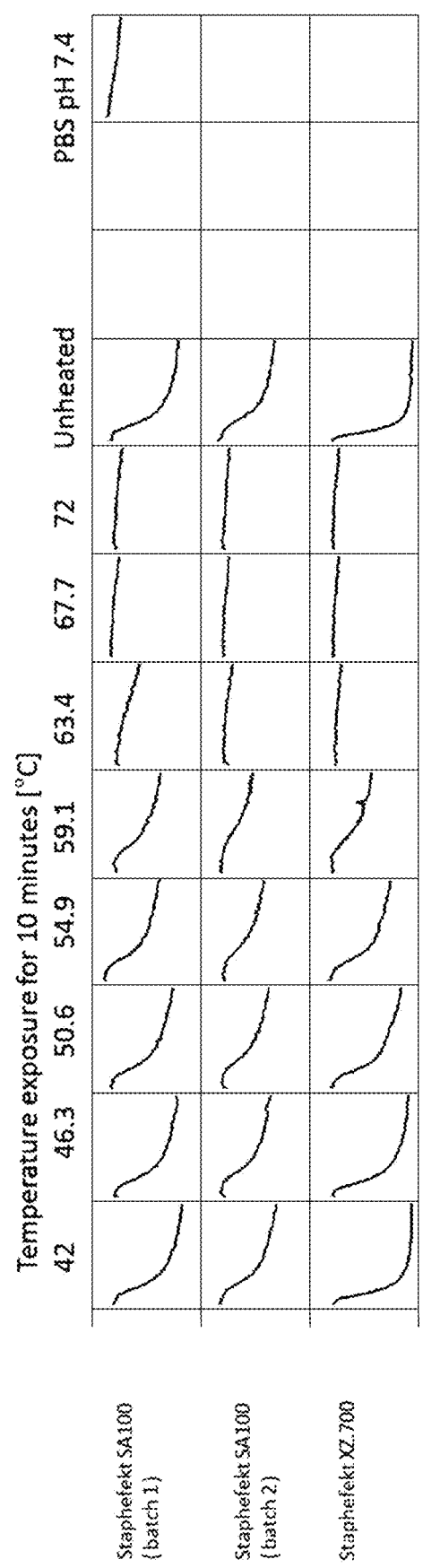

FIG. 3. Turbidity reduction assays comparing SA.100 (upper pane and mid pane) with XZ.700 (lower pane).

EXAMPLES

Materials and Methods

Bacterial Strains, Culture Conditions, Phages and Plasmids

*E. coli* XL1BlueMRF and *E. coli* Sure was used for the over-expression of polypeptides according to the invention, essentially as in WO2013/169102. Both strains were cultured in LB-PE medium at 30° C. with 100 µg/ml ampicillin and 30 µg/ml tetracycline for plasmid selection.

DNA Techniques and Cloning Procedures

Standard techniques according to Sambrook, Maniatis et al. (1989) were employed for cloning.

Expression and Purification of Recombinant Endolysin Polypeptides

Protein overexpression and partial purification was essentially done as previously described by others (Loessner et al., 1996, Schmelcher et al., 2010). In brief, plasmid bearing *E. coli* were grown in 250 ml modified LB medium (15 g/l tryptose, 8 g/l yeast extract, 5 g/l NaCl, pH 7.8) to an optical density at 600 nm (OD600 nm) of 0.4 to 0.6 and induced with 1 mM IPTG. Cells were further incubated for 4 hours at 30° C., or 18 hours at 20° C., cooled to 4° C., and harvested by centrifugation. Cell pellets were suspended in 5 ml immobilization buffer (50 mM $NaH_2PO_4$, 500 mM NaCl, 5 mM imidazole, 0.1% polysorbate20, pH 7.4). Cytosolic *E. coli* contents containing soluble recombinant proteins were liberated by a double passage through a French Pressure Cell Press (1200 psi, SLM Aminco, Urbana, Ill., U.S.) operated at 1200 psi. Other downstream processing steps included removal of insoluble cell debris by centrifugation, filter sterilization (0.2 µm PES membrane, Millipore), and Immobilized Metal Affinity Chromatography (IMAC) purification using MicroBiospin (Bio-Rad, Hercules, Calif., U.S.) columns packet with low density Ni-NTA Superflow resin (Chemie Brunschwig AG, Basel, Switzerland). Ni-NTA immobilized proteins were on-column gravity flow washed with 5-10 column volumes immobilization buffer. Protein fractions were then eluted with elution buffer (50 mM $NaH_2PO_4$, 500 mM NaCl, 125 mM imidazole, 0.1% polysorbate20, pH 7.4) and dialyzed against two changes of dialysis buffer (50 mM $NaH_2PO_4$, 100 mM NaCl, 0.1% polysorbate20, pH 7.4). Protein concentrations were defined in a NanoDrop ND-1000 spectrophotmeter, corrected for specific absorbance at 280 nm as calculated from the primary amino acid sequence with Vector NTI software (Invitrogen, Carlsbad, Calif., U.S.) and estimated for purity by SDS-PAGE. Aliquots were stored at −20° C. mixed with 50% glycerol.

Lyophilization of Recombinant Proteins

IMAC purified proteins were dialyzed against 3 changes of 300 ml lyophilization buffer (50 mM phosphate or Tris, 500 mM sucrose, 200 mM mannitol, pH 7.4) aliquot and frozen in the gaseous phase of liquid nitrogen. The freeze-drying was done at −40° C. and vacuum at 75 mTorr for 60 minutes, followed by increasing temperature during 5 hours to −10° C. and another 60 minutes at −10° C. at the same vacuum levels. As final step, temperature was increased to 25° C. during 10 hours. Samples were reconstituted prior to testing in lysis assays by the addition of water.

Turbidity Lysis Assays

Substrate cells for lytic activity assays were grown to an optical density at 595 nm (OD595) of 0.4, washed twice with PBST pH 7.4 and re-suspended in 15% glycerol containing PBS buffer pH 7.4 concentrating it at the same time 100 fold. The cells were stored at −20° C. For further use in binding or lytic activity assays the cells were thaw, washed with PBS pH 7.4 and diluted to an OD595 of 1±0.05. In standard lytic activity assays protein samples were diluted to equimolar amounts and distributed in transparent 96-well tissue culture test plates (SPL life sciences, Pocheon, Korea). Substrate cells were added to a final volume and drop in optical density at 595 nm (OD595 nm) were recorded for about 1 hour at 37° C.

Decrease in optical density at 595 nm (OD595) was measured using a Victor3 1420 Multilabel Counter instrument (Perkin Elmer) during 1 hour. Plates were shaken vigorously for 1 second (double orbit, 0.1 mm diameter) after every single read out. As positive control served N-terminal 6× His tagged Lysostaphin (HLST), commercially available Lysostaphin (recombinant, *E. coli* originated, Sigma). As negative control we applied MilliQ water.

Minimal Inhibitory Concentration (MIC) Assay

Two-fold serial dilutions (2000 nM to 4 nM) of endolysin in casein peptone soybean flour peptone broth (CASO broth (Carl Roth, Germany)) were distributed in sterile crystal clear 96-well plates at 100 μl/well. *S. aureus* Newbold were grown in CASO broth to mid log phase (OD600 nm ~0.5) and diluted with fresh CASO broth to ~1E+6 cfu/ml. The cells were then distributed in the endolysin containing wells resulting in endolysin concentrations of 1000 nM to 2 nM and ~10E+5 cfu/well. The 96-well plates were covered with the lid and incubated for 20 hours at 30° C. Images were takes using a gel scanner. As positive control served CASO broth without endolysin, and as negative control CASO broth without *S. aureus* cells was used.

Results

Determination of Specific Activity of an Endolysin Polypeptide According to the Invention by Minimal Inhibitory Concentration Analysis The specific activity of XZ.700, an endolysin polypeptide with an amino acid sequence according to SEQ ID NO: 2 was compared to that of SA.100, a reference endolysin polypeptide with an amino acid sequence according to SEQ ID NO: 1. The results are depicted in FIG. 1. MIC values were obtained by exposure of 2-3E+5 cfu *S. aureus* Newbold to serial dilutions of Staphefekt in a 200 μl format. The image was taken after 20 h incubation in CASO medium. The MIC value of SA.100 was 62.5 nM and MIC value of XZ.700 was 15.6 nM in three independent assays; i.e. the MIC value of XZ.700 is four-fold lower that of SA.100, indicative of a four-fold higher specific activity of XZ.700.

Determination of Thermal Stability and Specific Activity of an Endolysin Polypeptide According to the Invention by Turbidity Assay The thermal stability and specific activity of XZ.700, an endolysin polypeptide with an amino acid sequence according to SEQ ID NO: 2 were compared to those of SA.100, a reference endolysin polypeptide with an amino acid sequence according to SEQ ID NO: 1. In brief, 200 mM of SA.100 and XZ.700 were subjected to 10 minutes heat exposure (X-axis) followed by cooling on ice. The relative activity in view of SA.100 at 20 degrees Celsius was subsequently determined by turbidity lysis assay. It can clearly be observed in FIG. 2 that the activity of XZ.700 is somewhat lower than SA.100 from about 55 degrees Celsius and higher, whereas the activity of XZ.700 is significantly higher than SA.100 up to about 55 degrees Celsius. At room temperature, the activity of ZX.700 is about 70% higher than SA.100.

Specific activity and thermal stability were also determined using a kinetic assay. XZ.700 and SA.100 at concentrations of 200 nM were heat exposed between 42 degrees Celsius and 72 degrees Celsius for 10 minutes in PBS buffer in a gradient thermocycler. After subsequent cooling on ice, lysis kinetics in standard dynamic turbidity reduction assays were recorded at 100 nM protein concentrations against *S. aureus* SA.113 in PBS buffer pH 7.4. The lysis curves are depicted in FIG. 3 and show optical density reductions (Y-axis, initial OD600 nm ~1) over time (X-axis, duration 1 h). It can clearly be observed that up to 60 degrees Celsius ZX.700 has a significantly steeper curve than SA.100, indicating higher specific activity.

Immunogenicity Prediction of an Endolysin Polypeptide According to the Invention.

Immunogenicity predictions were performed on the XZ.700 and SA.100 polypeptide sequences (SEQ ID NO: 1 and SEQ ID NO: 2, respectively) using the tools.immuneepitope.org/bcell/webpage with parameters: centre position 4, window size 7, and threshold 1.0. The results are depicted in Table 1. It is clear that the immunogenic peptide fragment "VKELKHIYSNH" (position 197-207 in SA.100) is not present in XZ.700.

Altogether, in this non-limiting example, it was demonstrated that endolysin polypeptide according to the invention XZ.700 has a higher specific activity and lower immunogenicity than prior art endolysin polypeptide SA.100.

TABLE 1

Kolaskar & Tongaonkar Immunogenicity prediction of peptides present in Staphefekt SA.100 (left) and Staphefekt XZ.700 (right).

| Predicted peptides: SA.100 | | | | Predicted peptides: XZ.700 | | | |
|---|---|---|---|---|---|---|---|
| No. | Start | End | Peptide | No. | Start | End | Peptide |
| 1 | 5 | 10 | HEHSAQ | 1 | 5 | 10 | HEHSAQ |
| 2 | 21 | 27 | YGPYPLG | 2 | 21 | 27 | YGPYPLG |
| 3 | 44 | 49 | TPVKAI | 3 | 44 | 49 | TPVKAI |
| 4 | 51 | 57 | SGKIVEA | 4 | 51 | 57 | SGKIVEA |
| 5 | 81 | 100 | YMHLSKYNVKVGDYVKAGQI | 5 | 81 | 100 | YMHLSKYNVKVGDYVKAGQI |
| 6 | 111 | 119 | TAPHLHFQR | 6 | 111 | 119 | TAPHLHFQR |
| 7 | 133 | 139 | MPFLKSA | 7 | 133 | 139 | MPFLKSA |
| 8 | 169 | 175 | SQVCSGL | 8 | 157 | 163 | KHIYSNH |
| 9 | 197 | 207 | VKELKHIYSNH | | | | |
| 10 | 215 | 227 | APKPSIQGVVIHN | 9 | 171 | 183 | APKPSIQGVVIHN |
| 11 | 234 | 242 | PSQYLPWLY | 10 | 190 | 198 | PSQYLPWLY |
| 12 | 252 | 259 | NGWASVYA | 11 | 208 | 215 | NGWASVYA |
| 13 | 264 | 276 | VLWYHPTDYVEWH | 12 | 220 | 232 | VLWYHPTDYVEWH |
| 14 | 287 | 295 | IGFEVCESY | 13 | 243 | 251 | IGFEVCESY |
| 15 | 311 | 325 | TLKVAADVMKSYGLP | 14 | 267 | 281 | TLKVAADVMKSYGLP |
| 16 | 331 | 336 | VRLHNE | 15 | 287 | 292 | VRLHNE |
| 17 | 339 | 354 | GTSCPHRSWDLHVGKG | 16 | 295 | 310 | GTSCPHRSWDLHVGKG |
| 18 | 369 | 376 | FIKRIKHY | 17 | 325 | 332 | FIKRIKHY |
| 19 | 381 | 390 | KLEVSKAATI | 18 | 337 | 346 | KLEVSKAATI |
| 20 | 392 | 399 | QSDVKQEV | 19 | 348 | 355 | QSDVKQEV |
| 21 | 405 | 410 | KQIVKA | 20 | 361 | 366 | KQIVKA |
| 22 | 423 | 436 | KAEHASFTVTAPEG | 21 | 379 | 392 | KAEHASFTVTAPEG |
| 23 | 450 | 457 | QAGVLQKG | 22 | 406 | 413 | QAGVLQKG |
| 24 | 462 | 476 | YDEVQKFDGHVWVSW | 23 | 418 | 432 | YDEVQKFDGHVWVSW |

SEQUENCES

SEQ ID NO: 1
MAATHEHSAQWLNNYKKGYGYGPYPLGINGGMHYGVDFFMNIGTP
VKAISSGKIVEAGWSNYGGGNQIGLIENDGVHRQWYMHLSKYNVK
VGDYVKAGQIIGWSGSTGYSTAPHLHFQRMVNSFSNSTAQDPMPF
LKSAGYGKAGGTVTPTPNTGELLRPKDAKKDEKSQVCSGLAMEKY
DITNLNAKQDKSKNGSVKELKHIYSNHIKGNKITAPKPSIQGVVI
HNDYGSMTPSQYLPWLYARENNGTHVNGWASVYANRNEVLWYHPT
DYVEWHCGNQWANANLIGFEVCESYPGRISDKLFLENEEATLKVA
ADVMKSYGLPVNRNTVRLHNEFFGTSCPHRSWDLHVGKGEPYTTT
NINKMKDYFIKRIKHYYDGGKLEVSKAATIKQSDVKQEVKKQEAK
QIVKATDWKQNKDGIWYKAEHASFTVTAPEGIITRYKGPWTGHPQ
AGVLQKGQTIKYDEVQKFDGHVWVSWETFEGETVYMPVRTWDAKT
GKVGKLWGEIK

SEQ ID NO: 2
MAATHEHSAQWLNNYKKGYGYGPYPLGINGGMHYGVDFFMNIGTP
VKAISSGKIVEAGWSNYGGGNQIGLIENDGVHRQWYMHLSKYNVK
VGDYVKAGQIIGWSGSTGYSTAPHLHFQRMVNSFSNSTAQDPMPF
LKSAGYGKAGGTVTPTPNTGLKHIYSNHIKGNKITAPKPSIQGVV
IHNDYGSMTPSQYLPWLYARENNGTHVNGWASVYANRNEVLWYHP
TDYVEWHCGNQWANANLIGFEVCESYPGRISDKLFLENEEATLKV
AADVMKSYGLPVNRNTVRLHNEFFGTSCPHRSWDLHVGKGEPYTT
TNINKMKDYFIKRIKHYYDGGKLEVSKAATIKQSDVKQEVKKQEA
KQIVKATDWKQNKDGIWYKAEHASFTVTAPEGIITRYKGPWTGHP
QAGVLQKGQTIKYDEVQKFDGHVWVSWETFEGETVYMPVRTWDAK
TGKVGKLWGEIK

The invention claimed is:

1. A method of treatment of atopic dermatitis or eczema comprising administrating to a subject in need thereof an endolysin polypeptide specific for *Staphylococcus*, said polypeptide comprising:
   a polypeptide with an amino acid sequence that has at least 90% sequence identity with SEQ ID NO: 2 over its entire length, or
   a polypeptide with an amino acid sequence that has at least 90% sequence identity with SEQ ID NO: 1 and having a truncation of at least 5, 10, 20, 30, or 40 amino acids in the region of amino acids 156 to 199 of SEQ ID NO: 1, wherein the endolysin polypeptide has enhanced specific activity and/or reduced immunogenicity than an endolysin polypeptide with the amino acid sequence according to SEQ ID NO: 1, and wherein the polypeptide is a synthetic molecule.

2. The method of treatment according to claim 1, wherein the endolysin polypeptide comprises the amino acid sequence according to SEQ ID NO: 2.

3. A method of treatment according to claim 1, wherein the endolysin polypeptide is administered within a composition.

4. The method of treatment according to claim 3, wherein the composition further comprises a pharmaceutically acceptable excipient.

5. The method of treatment according to claim 3, wherein the composition further comprises an additional active ingredient.

6. The method of treatment according to claim 5, wherein the additional active ingredient is selected from the group consisting of a bacteriophage or phage, a phage endolysin derived from such phage and an antibiotic.

7. The method of treatment according to claim 3, wherein the composition is in liquid, solid, semi-liquid or semi-solid form.

8. The method of treatment according to claim 3, wherein the subject is an animal subject.

9. The method of treatment according to claim 8, wherein the subject is cattle or a domestic animal, or wherein the subject is a human.

* * * * *

SEQUENCE LISTING

<160> NUMBER OF SEQ ID NOS: 26

<210> SEQ ID NO 1
<211> LENGTH: 506
<212> TYPE: PRT

<213> ORGANISM: Artificial Sequence
<220> FEATURE:
<223> OTHER INFORMATION: Chimeric polypeptide

<400> SEQUENCE: 1

```
Met Ala Ala Thr His Glu His Ser Ala Gln Trp Leu Asn Asn Tyr Lys
1               5                   10                  15

Lys Gly Tyr Gly Tyr Gly Pro Tyr Pro Leu Gly Ile Asn Gly Gly Met
            20                  25                  30

His Tyr Gly Val Asp Phe Phe Met Asn Ile Gly Thr Pro Val Lys Ala
        35                  40                  45

Ile Ser Ser Gly Lys Ile Val Glu Ala Gly Trp Ser Asn Tyr Gly Gly
50                  55                  60

Gly Asn Gln Ile Gly Leu Ile Glu Asn Asp Gly Val His Arg Gln Trp
65                  70                  75                  80

Tyr Met His Leu Ser Lys Tyr Asn Val Lys Val Gly Asp Tyr Val Lys
                85                  90                  95

Ala Gly Gln Ile Ile Gly Trp Ser Gly Ser Thr Gly Tyr Ser Thr Ala
            100                 105                 110

Pro His Leu His Phe Gln Arg Met Val Asn Ser Phe Ser Asn Ser Thr
        115                 120                 125

Ala Gln Asp Pro Met Pro Phe Leu Lys Ser Ala Gly Tyr Gly Lys Ala
130                 135                 140

Gly Gly Thr Val Thr Pro Thr Pro Asn Thr Gly Glu Leu Leu Arg Pro
145                 150                 155                 160

Lys Asp Ala Lys Lys Asp Glu Lys Ser Gln Val Cys Ser Gly Leu Ala
                165                 170                 175

Met Glu Lys Tyr Asp Ile Thr Asn Leu Asn Ala Lys Gln Asp Lys Ser
            180                 185                 190

Lys Asn Gly Ser Val Lys Glu Leu Lys His Ile Tyr Ser Asn His Ile
        195                 200                 205

Lys Gly Asn Lys Ile Thr Ala Pro Lys Pro Ser Ile Gln Gly Val Val
210                 215                 220

Ile His Asn Asp Tyr Gly Ser Met Thr Pro Ser Gln Tyr Leu Pro Trp
225                 230                 235                 240

Leu Tyr Ala Arg Glu Asn Asn Gly Thr His Val Asn Gly Trp Ala Ser
                245                 250                 255

Val Tyr Ala Asn Arg Asn Glu Val Leu Trp Tyr His Pro Thr Asp Tyr
            260                 265                 270

Val Glu Trp His Cys Gly Asn Gln Trp Ala Asn Ala Asn Leu Ile Gly
        275                 280                 285

Phe Glu Val Cys Glu Ser Tyr Pro Gly Arg Ile Ser Asp Lys Leu Phe
290                 295                 300

Leu Glu Asn Glu Glu Ala Thr Leu Lys Val Ala Ala Asp Val Met Lys
305                 310                 315                 320

Ser Tyr Gly Leu Pro Val Asn Arg Asn Thr Val Arg Leu His Asn Glu
                325                 330                 335

Phe Phe Gly Thr Ser Cys Pro His Arg Ser Trp Asp Leu His Val Gly
            340                 345                 350

Lys Gly Glu Pro Tyr Thr Thr Thr Asn Ile Asn Lys Met Lys Asp Tyr
        355                 360                 365

Phe Ile Lys Arg Ile Lys His Tyr Tyr Asp Gly Gly Lys Leu Glu Val
370                 375                 380

Ser Lys Ala Ala Thr Ile Lys Gln Ser Asp Val Lys Gln Glu Val Lys
```

```
385                 390                 395                 400
Lys Gln Glu Ala Lys Gln Ile Val Lys Ala Thr Asp Trp Lys Gln Asn
                405                 410                 415

Lys Asp Gly Ile Trp Tyr Lys Ala Glu His Ala Ser Phe Thr Val Thr
                420                 425                 430

Ala Pro Glu Gly Ile Ile Thr Arg Tyr Lys Gly Pro Trp Thr Gly His
                435                 440                 445

Pro Gln Ala Gly Val Leu Gln Lys Gly Gln Thr Ile Lys Tyr Asp Glu
    450                 455                 460

Val Gln Lys Phe Asp Gly His Val Trp Val Ser Trp Glu Thr Phe Glu
465                 470                 475                 480

Gly Glu Thr Val Tyr Met Pro Val Arg Thr Trp Asp Ala Lys Thr Gly
                485                 490                 495

Lys Val Gly Lys Leu Trp Gly Glu Ile Lys
                500                 505
```

<210> SEQ ID NO 2
<211> LENGTH: 462
<212> TYPE: PRT
<213> ORGANISM: Artificial Sequence
<220> FEATURE:
<223> OTHER INFORMATION: Chimeric polypeptide

<400> SEQUENCE: 2

```
Met Ala Ala Thr His Glu His Ser Ala Gln Trp Leu Asn Asn Tyr Lys
1               5                   10                  15

Lys Gly Tyr Gly Tyr Gly Pro Tyr Pro Leu Gly Ile Asn Gly Gly Met
                20                  25                  30

His Tyr Gly Val Asp Phe Phe Met Asn Ile Gly Thr Pro Val Lys Ala
            35                  40                  45

Ile Ser Ser Gly Lys Ile Val Glu Ala Gly Trp Ser Asn Tyr Gly Gly
        50                  55                  60

Gly Asn Gln Ile Gly Leu Ile Glu Asn Asp Gly Val His Arg Gln Trp
65                  70                  75                  80

Tyr Met His Leu Ser Lys Tyr Asn Val Lys Val Gly Asp Tyr Val Lys
                85                  90                  95

Ala Gly Gln Ile Ile Gly Trp Ser Gly Ser Thr Gly Tyr Ser Thr Ala
                100                 105                 110

Pro His Leu His Phe Gln Arg Met Val Asn Ser Phe Ser Asn Ser Thr
            115                 120                 125

Ala Gln Asp Pro Met Pro Phe Leu Lys Ser Ala Gly Tyr Gly Lys Ala
        130                 135                 140

Gly Gly Thr Val Thr Pro Thr Pro Asn Thr Gly Leu Lys His Ile Tyr
145                 150                 155                 160

Ser Asn His Ile Lys Gly Asn Lys Ile Thr Ala Pro Lys Pro Ser Ile
                165                 170                 175

Gln Gly Val Val Ile His Asn Asp Tyr Gly Ser Met Thr Pro Ser Gln
            180                 185                 190

Tyr Leu Pro Trp Leu Tyr Ala Arg Glu Asn Asn Gly Thr His Val Asn
        195                 200                 205

Gly Trp Ala Ser Val Tyr Ala Asn Arg Asn Glu Val Leu Trp Tyr His
        210                 215                 220

Pro Thr Asp Tyr Val Glu Trp His Cys Gly Asn Gln Trp Ala Asn Ala
225                 230                 235                 240

Asn Leu Ile Gly Phe Glu Val Cys Glu Ser Tyr Pro Gly Arg Ile Ser
```

-continued

```
                245                 250                 255
Asp Lys Leu Phe Leu Glu Asn Glu Glu Ala Thr Leu Lys Val Ala Ala
                260                 265                 270

Asp Val Met Lys Ser Tyr Gly Leu Pro Val Asn Arg Asn Thr Val Arg
            275                 280                 285

Leu His Asn Glu Phe Phe Gly Thr Ser Cys Pro His Arg Ser Trp Asp
        290                 295                 300

Leu His Val Gly Lys Gly Glu Pro Tyr Thr Thr Thr Asn Ile Asn Lys
305                 310                 315                 320

Met Lys Asp Tyr Phe Ile Lys Arg Ile Lys His Tyr Tyr Asp Gly Gly
                325                 330                 335

Lys Leu Glu Val Ser Lys Ala Ala Thr Ile Lys Gln Ser Asp Val Lys
            340                 345                 350

Gln Glu Val Lys Gln Glu Ala Lys Gln Ile Val Lys Ala Thr Asp
        355                 360                 365

Trp Lys Gln Asn Lys Asp Gly Ile Trp Tyr Lys Ala Glu His Ala Ser
370                 375                 380

Phe Thr Val Thr Ala Pro Gly Ile Ile Thr Arg Tyr Lys Gly Pro
385                 390                 395                 400

Trp Thr Gly His Pro Gln Ala Gly Val Leu Gln Lys Gly Gln Thr Ile
                405                 410                 415

Lys Tyr Asp Glu Val Gln Lys Phe Asp Gly His Val Trp Val Ser Trp
            420                 425                 430

Glu Thr Phe Glu Gly Lys Thr Val Tyr Met Pro Val Arg Thr Trp Asp
        435                 440                 445

Ala Lys Thr Gly Lys Val Gly Lys Leu Trp Gly Glu Ile Lys
        450                 455                 460
```

<210> SEQ ID NO 3
<211> LENGTH: 6
<212> TYPE: PRT
<213> ORGANISM: Artificial Sequence
<220> FEATURE:
<223> OTHER INFORMATION: Peptide

<400> SEQUENCE: 3

```
His Glu His Ser Ala Gln
1               5
```

<210> SEQ ID NO 4
<211> LENGTH: 7
<212> TYPE: PRT
<213> ORGANISM: Artificial Sequence
<220> FEATURE:
<223> OTHER INFORMATION: Peptide

<400> SEQUENCE: 4

```
Tyr Gly Pro Tyr Pro Leu Gly
1               5
```

<210> SEQ ID NO 5
<211> LENGTH: 6
<212> TYPE: PRT
<213> ORGANISM: Artificial Sequence
<220> FEATURE:
<223> OTHER INFORMATION: Peptide

<400> SEQUENCE: 5

```
Thr Pro Val Lys Ala Ile
1               5
```

<210> SEQ ID NO 6
<211> LENGTH: 7
<212> TYPE: PRT
<213> ORGANISM: Artificial Sequence
<220> FEATURE:
<223> OTHER INFORMATION: Peptide

<400> SEQUENCE: 6

Ser Gly Lys Ile Val Glu Ala
1               5

<210> SEQ ID NO 7
<211> LENGTH: 20
<212> TYPE: PRT
<213> ORGANISM: Artificial Sequence
<220> FEATURE:
<223> OTHER INFORMATION: Peptide

<400> SEQUENCE: 7

Tyr Met His Leu Ser Lys Tyr Asn Val Lys Val Gly Asp Tyr Val Lys
1               5                   10                  15

Ala Gly Gln Ile
            20

<210> SEQ ID NO 8
<211> LENGTH: 9
<212> TYPE: PRT
<213> ORGANISM: Artificial Sequence
<220> FEATURE:
<223> OTHER INFORMATION: Peptide

<400> SEQUENCE: 8

Thr Ala Pro His Leu His Phe Gln Arg
1               5

<210> SEQ ID NO 9
<211> LENGTH: 7
<212> TYPE: PRT
<213> ORGANISM: Artificial Sequence
<220> FEATURE:
<223> OTHER INFORMATION: Peptide

<400> SEQUENCE: 9

Met Pro Phe Leu Lys Ser Ala
1               5

<210> SEQ ID NO 10
<211> LENGTH: 7
<212> TYPE: PRT
<213> ORGANISM: Artificial Sequence
<220> FEATURE:
<223> OTHER INFORMATION: Peptide

<400> SEQUENCE: 10

Ser Gln Val Cys Ser Gly Leu
1               5

<210> SEQ ID NO 11
<211> LENGTH: 11
<212> TYPE: PRT
<213> ORGANISM: Artificial Sequence
<220> FEATURE:
<223> OTHER INFORMATION: Peptide

<400> SEQUENCE: 11

Val Lys Glu Leu Lys His Ile Tyr Ser Asn His
1               5                   10

<210> SEQ ID NO 12
<211> LENGTH: 13
<212> TYPE: PRT
<213> ORGANISM: Artificial Sequence
<220> FEATURE:
<223> OTHER INFORMATION: Peptide

<400> SEQUENCE: 12

Ala Pro Lys Pro Ser Ile Gln Gly Val Val Ile His Asn
1               5                   10

<210> SEQ ID NO 13
<211> LENGTH: 9
<212> TYPE: PRT
<213> ORGANISM: Artificial Sequence
<220> FEATURE:
<223> OTHER INFORMATION: Peptide

<400> SEQUENCE: 13

Pro Ser Gln Tyr Leu Pro Trp Leu Tyr
1               5

<210> SEQ ID NO 14
<211> LENGTH: 8
<212> TYPE: PRT
<213> ORGANISM: Artificial Sequence
<220> FEATURE:
<223> OTHER INFORMATION: Peptide

<400> SEQUENCE: 14

Asn Gly Trp Ala Ser Val Tyr Ala
1               5

<210> SEQ ID NO 15
<211> LENGTH: 13
<212> TYPE: PRT
<213> ORGANISM: Artificial Sequence
<220> FEATURE:
<223> OTHER INFORMATION: Peptide

<400> SEQUENCE: 15

Val Leu Trp Tyr His Pro Thr Asp Tyr Val Glu Trp His
1               5                   10

<210> SEQ ID NO 16
<211> LENGTH: 9
<212> TYPE: PRT
<213> ORGANISM: Artificial Sequence
<220> FEATURE:
<223> OTHER INFORMATION: Peptide

<400> SEQUENCE: 16

Ile Gly Phe Glu Val Cys Glu Ser Tyr
1               5

<210> SEQ ID NO 17
<211> LENGTH: 15
<212> TYPE: PRT
<213> ORGANISM: Artificial Sequence
<220> FEATURE:
<223> OTHER INFORMATION: Peptide

<400> SEQUENCE: 17

Thr Leu Lys Val Ala Ala Asp Val Met Lys Ser Tyr Gly Leu Pro

-continued

```
1               5                   10                  15

<210> SEQ ID NO 18
<211> LENGTH: 6
<212> TYPE: PRT
<213> ORGANISM: Artificial Sequence
<220> FEATURE:
<223> OTHER INFORMATION: Peptide

<400> SEQUENCE: 18

Val Arg Leu His Asn Glu
1               5

<210> SEQ ID NO 19
<211> LENGTH: 16
<212> TYPE: PRT
<213> ORGANISM: Artificial Sequence
<220> FEATURE:
<223> OTHER INFORMATION: Peptide

<400> SEQUENCE: 19

Gly Thr Ser Cys Pro His Arg Ser Trp Asp Leu His Val Gly Lys Gly
1               5                   10                  15

<210> SEQ ID NO 20
<211> LENGTH: 8
<212> TYPE: PRT
<213> ORGANISM: Artificial Sequence
<220> FEATURE:
<223> OTHER INFORMATION: Peptide

<400> SEQUENCE: 20

Phe Ile Lys Arg Ile Lys His Tyr
1               5

<210> SEQ ID NO 21
<211> LENGTH: 10
<212> TYPE: PRT
<213> ORGANISM: Artificial Sequence
<220> FEATURE:
<223> OTHER INFORMATION: Peptide

<400> SEQUENCE: 21

Lys Leu Glu Val Ser Lys Ala Ala Thr Ile
1               5                   10

<210> SEQ ID NO 22
<211> LENGTH: 8
<212> TYPE: PRT
<213> ORGANISM: Artificial Sequence
<220> FEATURE:
<223> OTHER INFORMATION: Peptide

<400> SEQUENCE: 22

Gln Ser Asp Val Lys Gln Glu Val
1               5

<210> SEQ ID NO 23
<211> LENGTH: 6
<212> TYPE: PRT
<213> ORGANISM: Artificial Sequence
<220> FEATURE:
<223> OTHER INFORMATION: Peptide

<400> SEQUENCE: 23

Lys Gln Ile Val Lys Ala
1               5
```

```
<210> SEQ ID NO 24
<211> LENGTH: 14
<212> TYPE: PRT
<213> ORGANISM: Artificial Sequence
<220> FEATURE:
<223> OTHER INFORMATION: Peptide

<400> SEQUENCE: 24

Lys Ala Glu His Ala Ser Phe Thr Val Thr Ala Pro Glu Gly
1               5                  10

<210> SEQ ID NO 25
<211> LENGTH: 8
<212> TYPE: PRT
<213> ORGANISM: Artificial Sequence
<220> FEATURE:
<223> OTHER INFORMATION: Peptide

<400> SEQUENCE: 25

Gln Ala Gly Val Leu Gln Lys Gly
1               5

<210> SEQ ID NO 26
<211> LENGTH: 15
<212> TYPE: PRT
<213> ORGANISM: Artificial Sequence
<220> FEATURE:
<223> OTHER INFORMATION: Peptide

<400> SEQUENCE: 26

Tyr Asp Glu Val Gln Lys Phe Asp Gly His Val Trp Val Ser Trp
1               5                  10                  15
```